US00PP15058P2

(12) United States Plant Patent
Fear et al.

(10) Patent No.: US PP15,058 P2
(45) Date of Patent: Aug. 3, 2004

(54) BLACKBERRY PLANT NAMED 'DRISCOLL CARMEL'

(50) Latin Name: *Rubus L.*
Varietal Denomination: Driscoll Carmel

(75) Inventors: Carlos D. Fear, Aptos, CA (US); Gavin Sills, Watsonville, CA (US); Fred M. Cook, Aptos, CA (US); Richard E. Harrison, Aptos, CA (US)

(73) Assignee: Driscoll Strawberry Associates, Inc., Watsonville, CA (US)

( * ) Notice: Subject to any disclaimer, the term of this patent is extended or adjusted under 35 U.S.C. 154(b) by 74 days.

(21) Appl. No.: 10/306,454

(22) Filed: Nov. 27, 2002

(51) Int. Cl.[7] ..... A01H 5/00
(52) U.S. Cl. ..... Plt./203
(58) Field of Search ..... Plt./203

*Primary Examiner*—Anne Marie Grunberg
*Assistant Examiner*—Susan McCormick-Ewoldt
(74) *Attorney, Agent, or Firm*—Pennie & Edmonds LLP

(57) ABSTRACT

The present invention relates to a new and distinct cultivar of blackberry plant named Driscoll Carmel. The new cultivar is distinguished from other blackberry cultivars by its high productivity, early season, and low chill requirement. Driscoll Carmel produces fruit with improved quality and shipping characteristics over a long fruiting period. The new cultivar is distinguished from its seed parent by having better flavored fruit; it is distinguished from its pollen parent by its larger fruit.

2 Drawing Sheets

Latin name of the genus and species of the plant claimed: The variety is botanically identified as Rubus L. Subgenus Rubus.

1. BACKGROUND OF THE INVENTION

This invention relates to a new cultivar of blackberry called 'Driscoll Carmel'. The new cultivar was developed from hybridization of the unpatented female cultivar 'BY45.1' with the unpatented male selection 'BY63.2'. The parents were crossed in 1996, where after fruit and seed were collected to produce seedlings for field planting in Watsonville, Calif. in 1997. The new cultivar was selected in 1998 for its good flavor, fruit firmness and season of ripening. The cultivar has been asexually propagated in Watsonville, Calif., and reproduced true to type plants by in vitro shoot tip culture.

2. SUMMARY OF THE INVENTION

The present invention provides a new and distinct blackberry cultivar named 'Driscoll Carmel'. The variety is botanically identified as Rubus L. subgenus Rubus. The variety is a complex Rubus hybrid, which can be characterized as an erect tetraploid with considerable *R. alleghenien-sis* background with other species such as *R. trivialis, R. argutus R. procerus,* and *R. ulmifolious* also appearing in its background. The new cultivar produces a floricane crop which begins in late May and continues until mid-August. The new blackberry variety is distinguished from other varieties by a number of characteristics as set forth in Table 1. In particular, the new cultivar is distinguished by its low chill requirement, and its improved quality and shipping characteristics. Yield of the new cultivar is high when compared to many other varieties.

3. COMPARISON TO SIMILAR VARIETIES

The variety that we believe to be similar to 'Driscoll Carmel' from those known to us is 'Olallie', an unpatented variety. 'Driscoll Carmel' is particularly different from 'Olallie' by being later ripening, having less postharvest color reversion, having less acidic flavor, and having better fruit firmness. Further detailed comparison of 'Driscoll Carmel' to 'Olallie' and 'Chester' is presented in Table 1.

4. BRIEF DESCRIPTION OF THE DRAWINGS

The accompanying photographs show typical specimens of the fruit, leaves and shoot of the new cultivar, in color as nearly true as reasonably possible in color illustrations of this type.

Figure 1:
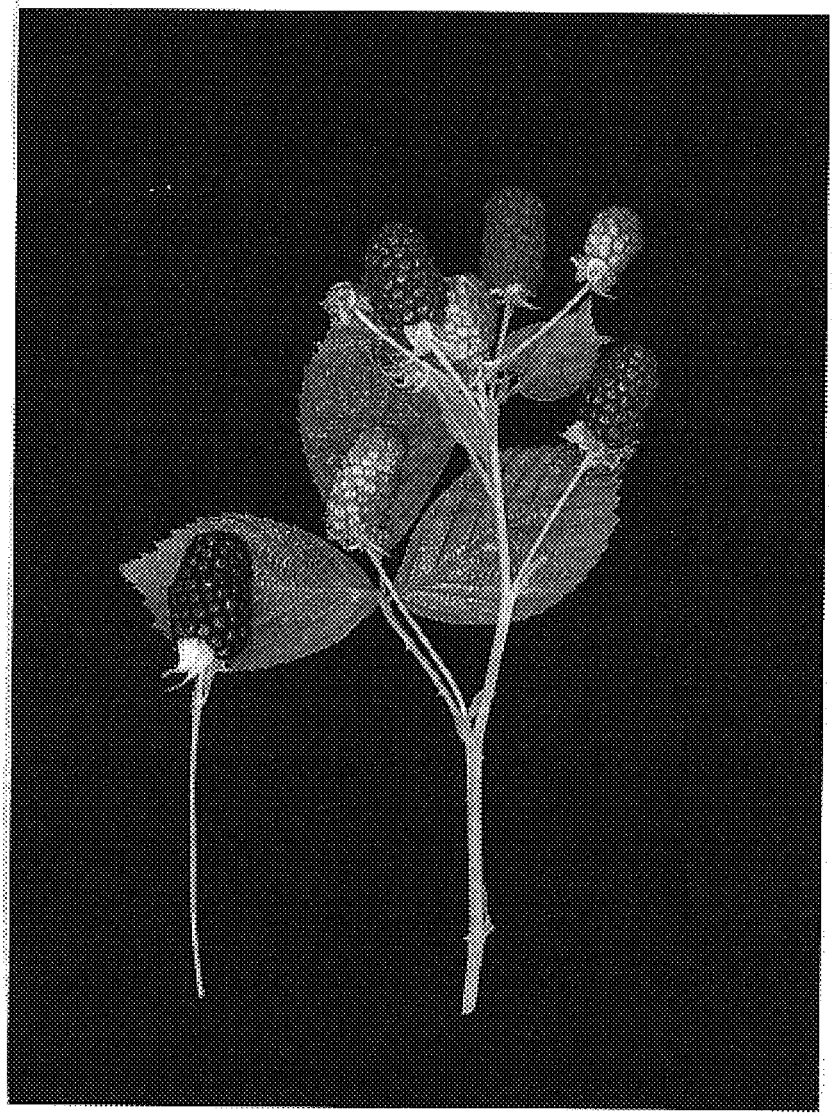

FIG. 1. is a photograph of a 'Driscoll Carmel' fruiting lateral with fruit in various stages of development.

Figure 2:
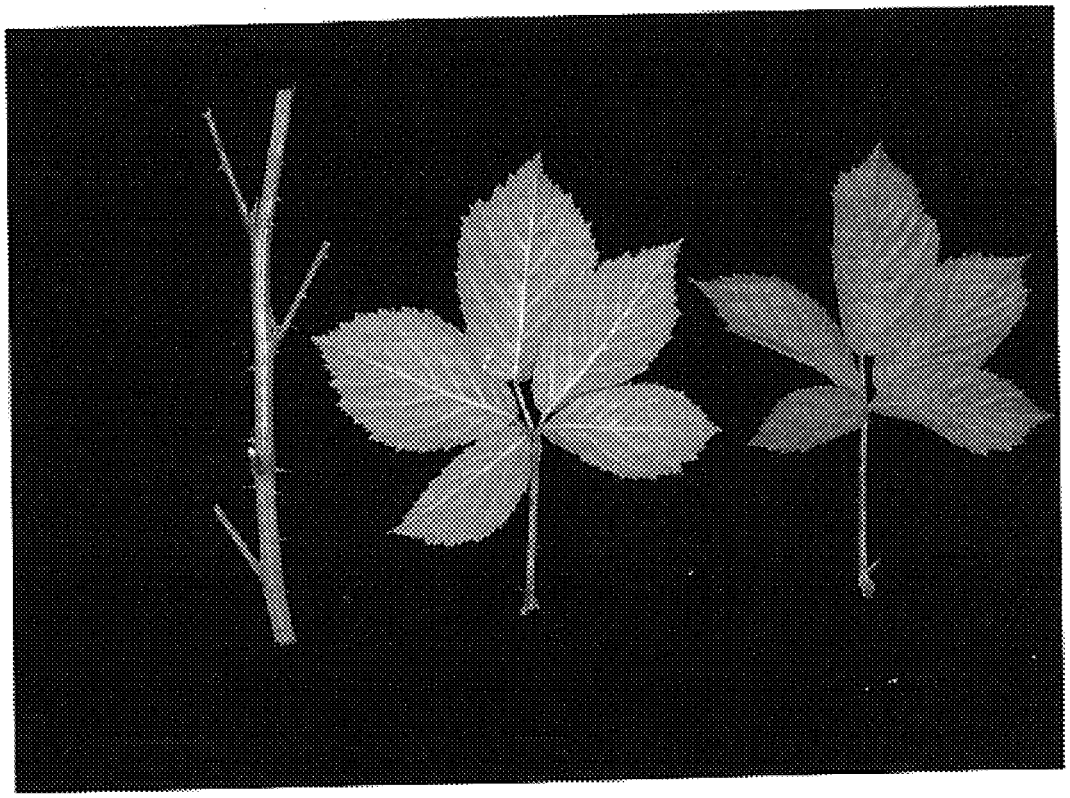

FIG. 2. is a photograph showing a close-up view of primocane leaves, mature leaf and stem of 'Driscoll Carmel'.

5. DESCRIPTION OF THE NEW VARIETY

The following detailed description of the new blackberry cultivar, 'Driscoll Carmel', is based upon recorded observations of 2–5 year old plants and fruit grown between 2000 and 2002 in Watsonville, Calif., and is believed to apply to plants of the 'Driscoll Carmel' cultivar grown in similar conditions of soil and climate elsewhere. Plants were planted in soil previously pre-plant fumigated and regularly fertilized and irrigated with drip irrigation. This description is in accordance with terminology used by the International Union for the Protection of New Varieties of Plants (UPOV). Throughout this specification, color names beginning with a small letter signify that the name of the color, as used in common speech, is aptly descriptive. Color data with a capital letter and an alphanumeric code indicate the most similar color designations as provided by The Royal Horticultural Society (R.H.S.) Colour Chart published by The Royal Horticultural Society of London, England. Color designations, color descriptions, and other phenotypical descriptions may deviate from the stated values and descriptions depending upon variation in environmental, seasonal, climatic and cultural conditions.

5.1 CHARACTERISTICS OF THE NEW VARIETY

Table 1 provides information on the plant and fruit characteristics of the new blackberry cultivar 'Driscoll Carmel' compared with characteristics of the unpatented blackberry cultivars 'Olallie' and 'Chester'. Both 'Olallie' and 'Chester' are currently important cultivars for fresh market shipping, and thus are comparable to the proposed use of the new invention, 'Driscoll Carmel'. Observations of 'Driscoll Carmel', 'Olallie', and 'Chester' were taken in side-by-side comparison between 2000 and in 2002.

Fruit of the new cultivar is particularly characterized and distinguished from other cultivars by its improved flavor and shipping characteristics. Drupelets of 'Driscoll Carmel' fruit show less postharvest color reversion compared to 'Olallie'.

'Driscoll Carmel' is highly productive and produces most of its crop in the middle part of the harvest season. Canes of 'Driscoll Carmel' are moderately vigorous, thorny and have buds with a low chill requirement. The average plant height is about 259 cm and the average plant spread is about 98 cm. The pigmentation of the young shoots is 146A. The sepals average about 9.5 mm in length and the average width of a sepal is about 5.3 mm. Sepal pigmentation color is 146B. The petiole pigmentation color on the upper surface is 146A.

The style pigmentation color is 143B, the average number of styles per flower is about 110, the anther pigmentation color is 155B, and the average number of anthers per flower is about 76. The number of petals per flower is five. The color of the seeds of 'Driscoll Carmel' is 152C and the average seed weight is 2.3 mg.

'Driscoll Carmel' is distinguished from its pollen parent, 'BY63.2' by having larger fruit and less postharvest color change. 'Driscoll Carmel' is distinguished from its seed parent, 'BY45.1', by having smaller, better flavored fruit and fewer thorns.

TABLE 1

PLANT CHARACTERISTICS OF 'DRISCOLL CARMEL'

| GENERAL | Driscoll Carmel | Chester | Olallie |
|---|---|---|---|
| Vigor | moderate | high | moderate-high |
| Growth habit | semi-erect | semi-erect | spreading |
| Productivity | high | high | high |
| Self fruitfulness | self-fruitful | self-fruitful | self-fruitful |
| Number of young shoots | medium | late | early |
| CANES | | | |
| Primocanes | | | |
| Young shoot pigmentation | medium | medium | weak |
| glucosity (waxy bloom) | absent or weak | medium | weak |
| cane cross section (from mid cane of primocane) | angular | angular to grooved | rounded to angular |
| dormant cane color | gray brown to purple | purple brown | brown to purple brown |
| Spines | present | absent | present |
| pigmentation | gray brown to purple 184-A | — | purple |
| color | 152-A | — | 187-A |
| density on young shoots | sparse | — | medium |
| attitude of tip | downward | — | downward to horizontal |
| size: Length (base to tip) (mm) | 4.3 | — | 3.0 |
| texture | smooth | — | heavy |

TABLE 1-continued

PLANT CHARACTERISTICS OF 'DRISCOLL CARMEL'

| GENERAL | Driscoll Carmel | Chester | Olallie |
|---|---|---|---|
| presence and distribution on petioles | present irregularly distributed | — | present irregularly distributed |
| Pubescence on canes | present | present | present |
| LEAVES | | | |
| Relief between veins | medium | weak | medium |
| Number of leaflets | usually 5 | usually 5 | sometimes 3, sometimes 5 |
| Glossiness | medium | medium | medium |
| Leaf cross section | concave | concave to flat | concave |
| Terminal leaflet | | | |
| length (cm) | 8.7 | 10.7 | 9.1 |
| width (cm) | 5.4 | 8.3 | 7.9 |
| shape | ovate | ovate | ovate |
| tip | acuminate | acuminate | acuminate |
| base | acute-rounded | cordate | cordate |
| margin | doubly serrated | doubly serrated | doubly serrated |
| Lateral leaflet | | | |
| overlap of lateral leaflets | yes | yes | yes |
| length (cm) | 7.9 | 9.2 | 8.4 |
| width (cm) | 4.5 | 6.4 | 6.3 |
| shape | ovate | ovate | ovate |
| tip | acuminate | acuminate | acuminate |
| base | oblique-acute | rounded | rounded |
| margin | doubly serrated | doubly serrated | doubly serrated |
| Rachis length (between terminal leaflet adjacent lateral leaflets) (cm) | 2.4 | 3.0 | 2.5 |
| Petiole | | | |
| length (cm) | 6.1 | 5.9 | 3.9 |
| pigmentation of upper surface | red purple/maroon | red purple/maroon | green to slightly pink |
| pigmentation of underside | yellow green | yellow green | yellow green |
| Stipule orientation | erect to clasping | erect | clasping to erect |
| Color | | | |
| face | 147-A | 146-A | 146-A |
| underside | 146-A | 146-A | 146-A |
| FLOWERS | | | |
| Flowering period time of beginning of flowering | early | very late | early |
| Flower size | medium | medium | medium |
| Flower diameter (cm) | 4.7 | 4.3 | 4.3 |
| Flower number (at 3rd node from tip of lateral, range and mean) | 4 to 7, mean 5.0 | 2 to 12, mean 9.5 | 3 to 6, mean 4.2 |
| Petal | | | |
| length (cm) | 2.3 | 2.0 | 2.0 |
| width (cm) | 1.7 | 1.4 | 1.3 |
| color | 155D | N74D | |
| Pedicel coloration | absent | weak | very weak |
| FRUIT | | | |
| Fruit harvest season | early-mid | late | early |
| Color | black | black | black |
| immature | 187-A | 187-A | 187-B |
| maturing | 202-A | 202-A | 202-A |
| mature fruit | 202-A | 202-A | 202-A |
| Glossiness | strong | medium | medium |
| Shape | ovate | round to ovate | narrow ovate |

TABLE 1-continued

PLANT CHARACTERISTICS OF 'DRISCOLL CARMEL'

| GENERAL | Driscoll Carmel | Chester | Olallie |
|---|---|---|---|
| Dimensions | | | |
| fruit size | medium | small | medium |
| length (cm) | 2.3 | 2.1 | 2.9 |
| width (cm) | 2.0 | 2.0 | 1.7 |
| Weight (g/fruit) | 6.2 | 3.6 | 4.7 |
| Soluble solids (%) | 11.9 | 9.6 | 10.4 |
| Titratable acidity (% as citric acid) (ml of added .1 N NaOH to pH 8.1) | 1.49 | 1.84 | 2.06 |
| Number of druplets per fruit | 61 | 46 | 86 |
| Firmness | firm | firm | soft |

5.2 NUCLEIC ACID FINGERPRINTING

Distinctive patterns of polymorphism can be detected using a variety of nucleic acid analysis methods. In one non-limiting example, molecular genetic maps can be produced using random amplified polymorphic DNA (RAPD) (Williams et al., 1990, "DNA polymorphisms amplified by arbitrary primers are useful as genetic markers", Nucleic Acids Res. 18(22):6531–5). Using a variety of oligonucleotide primers, alone or in combination, RAPD analysis of 'Driscoll Carmel', 'Chester', and 'Olallie' yielded DNA fragment patterns that uniquely distinguish each of these genetically distinct genotypes.

We claim:

1. A new and distinctive cultivar of blackberry plant, substantially as shown and described.

* * * * *